United States Patent
Berberich

(10) Patent No.: US 9,888,935 B2
(45) Date of Patent: Feb. 13, 2018

(54) MEDICAL CUTTING INSTRUMENT FOR CUTTING MUSCLES AND TENDONS

(75) Inventor: Sascha Berberich, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 492 days.

(21) Appl. No.: 13/547,809

(22) Filed: Jul. 12, 2012

(65) Prior Publication Data
US 2013/0018403 A1 Jan. 17, 2013

(30) Foreign Application Priority Data
Jul. 13, 2011 (DE) .................. 10 2011 107 176

(51) Int. Cl.
*A61B 17/3201* (2006.01)
*A61B 17/32* (2006.01)
(Continued)

(52) U.S. Cl.
CPC .......... *A61B 17/320016* (2013.01); *A61B 17/00008* (2013.01); *A61B 17/3205* (2013.01);
(Continued)

(58) Field of Classification Search
CPC .......... A61B 17/3201; A61B 17/29; A61B 17/320016; A61B 17/072; A61B 17/295; A61B 17/1608; A61B 2017/2927; A61B 2017/00353; A61B 2017/2905; A61B 2017/2926; A61B 2017/2929;
(Continued)

(56) References Cited

U.S. PATENT DOCUMENTS

| 253,359 A | 2/1882 | Ewing |
| 4,522,206 A | 6/1985 | Whipple et al. |

(Continued)

FOREIGN PATENT DOCUMENTS

| DE | 8421587 U1 | 10/1984 |
| DE | 10003020 A1 | 8/2001 |
| SU | 1456113 A1 | 2/1989 |

OTHER PUBLICATIONS

German Search Report; Application No. DE 10 2011 107 176.1; dated Apr. 20, 2012; 5 pages.
European Search Report Application No. 12005051.3 Completed: Feb. 22, 2017; dated Mar. 1, 2017 6 Pages.

*Primary Examiner* — Kathleen Holwerda
*Assistant Examiner* — Socrates L Boutsikaris
(74) *Attorney, Agent, or Firm* — Whitmyer IP Group LLC

(57) ABSTRACT

A medical cutting instrument for cutting muscles and tendons, having a shaft on whose distal end a tool is mounted consisting of two jaw members, such that one jaw member can be moved with respect to the other jaw member, and on whose proximal end a handle is mounted, such that the movable jaw member and the handle operatively interact by way of an actuation element, in such a way that the movable jaw member can be shifted by actuating the handle between a closed position and an opened position. The other jaw member is U-shaped such that the two parallel legs of the U are disposed diagonally to the instrument longitudinal axis and the opening of the U points toward one side of the other jaw member, so that the other jaw member can be pushed from the side onto the muscle/tendon tissue that is to be severed.

9 Claims, 4 Drawing Sheets

(51) Int. Cl.
*A61B 17/3205* (2006.01)
*A61B 17/295* (2006.01)
*A61B 17/00* (2006.01)

(52) U.S. Cl.
CPC ... *A61B 17/295* (2013.01); *A61B 2017/00969* (2013.01); *A61B 2017/32004* (2013.01)

(58) Field of Classification Search
CPC .. A61B 2017/2931; A61B 2017/07221; A61B 2017/320064; A61B 2017/2945; A61B 10/06; A61B 18/1442; A61B 18/1445; A61B 2018/1432
USPC ......... 606/174, 175, 83, 184, 170, 205, 207, 606/167, 206, 208, 51, 52, 159
See application file for complete search history.

(56) References Cited

U.S. PATENT DOCUMENTS

| | | | |
|---|---|---|---|
| 5,196,023 A * | 3/1993 | Martin | 606/148 |
| 5,282,816 A * | 2/1994 | Miller et al. | 606/167 |
| RE38,335 E * | 11/2003 | Aust | A61B 17/29 606/170 |
| 2001/0044635 A1* | 11/2001 | Niizeki | A61B 10/06 606/205 |
| 2002/0068935 A1 | 6/2002 | Kortenbach et al. | |
| 2003/0135275 A1* | 7/2003 | Garcia et al. | 623/17.11 |
| 2007/0066985 A1* | 3/2007 | Geitz et al. | 606/170 |
| 2008/0097482 A1* | 4/2008 | Bain | A61B 17/0469 606/144 |
| 2009/0043323 A1* | 2/2009 | Alleyne | A61B 17/3201 606/167 |
| 2011/0068147 A1* | 3/2011 | Racenet et al. | 227/180.1 |

* cited by examiner

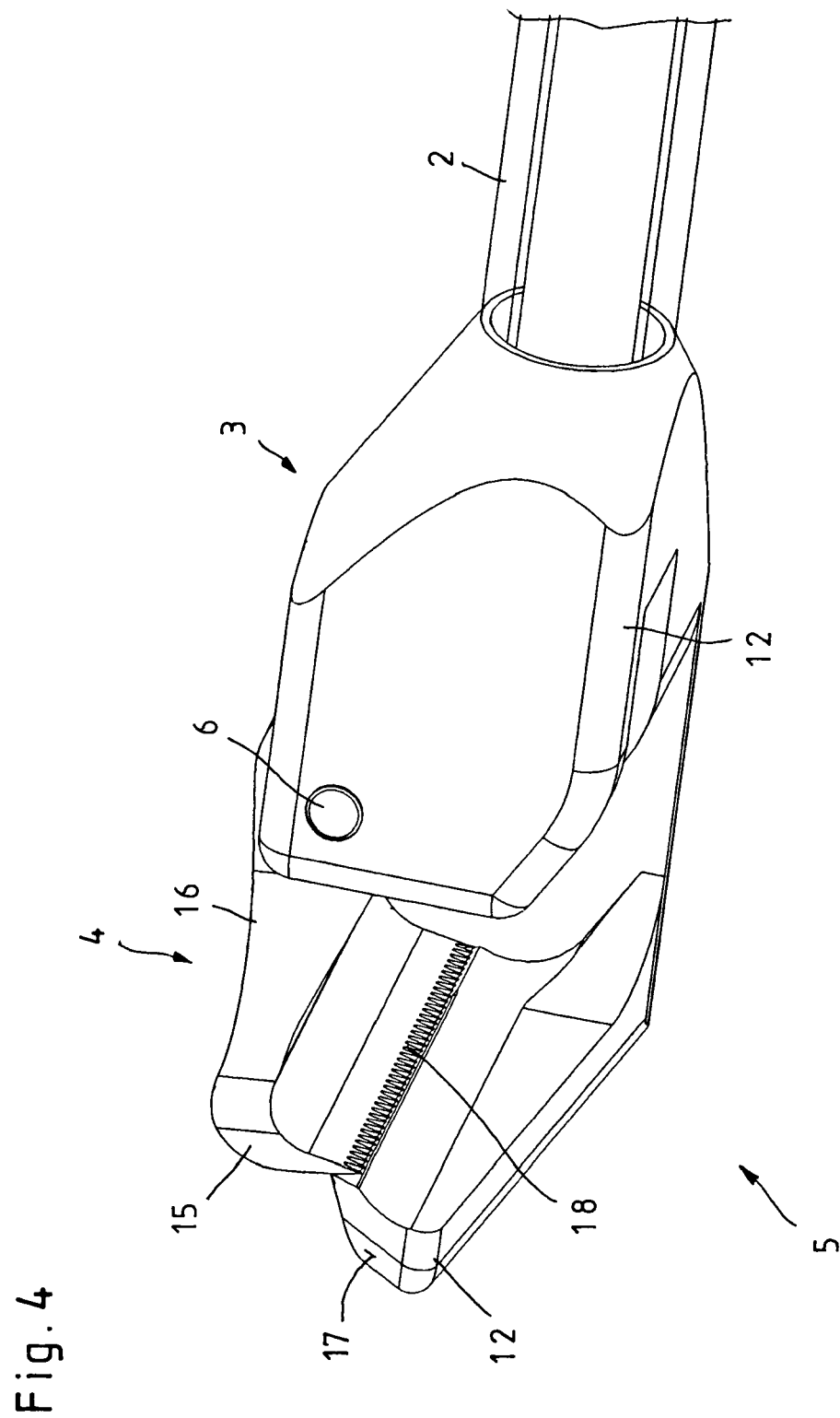

MEDICAL CUTTING INSTRUMENT FOR CUTTING MUSCLES AND TENDONS

CROSS-REFERENCE TO RELATED APPLICATIONS

The present application claims priority of German patent application No. 10 2011 107 176.1 filed on Jul. 13, 2011, the content of which is incorporated herein by reference.

FIELD OF THE INVENTION

The invention relates to a medical cutting instrument for cutting muscles and tendons, having a shaft on whose distal end a tool is disposed consisting of two jaw members, such that one jaw member is configured as a jaw member that is movable in relation to the other jaw member, and having a handle mounted on its proximal end such that the adjustable jaw member and the handle operatively interact with one another in such a way that the movable jaw member can be displaced by actuating the handle between a closed position and an opened position of the tool.

BACKGROUND OF THE INVENTION

Generic medical cutting instruments are used, for example, for the removal of tendons in order to use them as transplants to replace other destroyed tendons.

A medical cutting instrument for cutting muscles and tendons is known, for example, from U.S. Pat. No. 253,359. With this known instrument it is possible to make an incision that exposes a tendon, to salvage said tendon, and to remove a piece of this tendon tissue. In surgical practice, the use of the quadriceps tendon has proved useful as a transplant for replacing the anterior cruciate ligament. In the known surgical method for removing the quadriceps tendon transplant, the tendon is severed from the bones with a scalpel. The disadvantage with this known surgical method for removing the quadriceps tendon is the impossibility of controlled severing of the tendon.

SUMMARY OF THE INVENTION

It is consequently the object of the invention to provide a medical cutting instrument of the aforementioned type that is simple of handle and allows controlled severing of the muscle/tendon tissue in subcutaneous use.

This object is achieved according to the invention in a manner characterized by the features of Claim 1. Advantageous refinements of the invention are dealt with in the dependent claims.

The manner of achieving the object of the invention is characterized in that a rigid jaw member, in overhead view, is of U-shaped configuration in such a way that the two parallel legs of the rigid jaw member are disposed traverse to the instrument longitudinal axis and the opening of the rigid jaw member is directed toward a side of the rigid jaw member, so that the rigid jaw member can be pushed from the side onto the muscle/tendon tissue that is to be severed.

Owing to the inventive configuration of the other jaw member, which is open on one side, it is possible to push the rigid jaw member in controlled manner subcutaneously from the side onto the muscle/tendon tissue that is to be severed, in order to be able to sever the muscle/tendon tissue terminally.

According to a practical embodiment of the invention, it is proposed that at least on the movable jaw member a cutting edge should be configured that is mounted on the distal end of the movable jaw member, preferably oriented toward the other jaw member so that the muscle/tendon tissue disposed between the two jaw members is automatically severed upon the closing of the movable jaw member.

With a preferred embodiment of the invention it is proposed that V-shaped cutting edges should be mounted on both jaw members. The V-shaped configuration of the cutting edges has the effect that the tendon to be cut is first fastened on its outer side before then being definitively cut off in the central area. Thanks to this external fastening, a markedly better cutting result is achieved and undesired crushing, possibly resulting in pushing of the tendon, is prevented in the process of cutting.

It is further proposed with the invention that the cutting edge should be configured with comb-like teeth, so that the movable jaw member can be mounted onto the previously split muscle/tendon tissue and holds and guides it until the muscle-tendon tissue is severed by closing the jaw members.

To facilitate lateral pushing of the rigid jaw member onto the muscle/tendon tissue that is to be severed, it is proposed according to the invention that a run-up slope should be configured on the free end of the distal-side leg of the U-shaped other jaw member.

For adjusting and shifting the cutting depth, it is proposed with the invention that in the area of the handle a gear mechanism should be foreseen that forms a variable stop for the closing of the two jaw members with respect to one another and thus causes the shifting of the cutting depth. It is finally proposed with the invention that a scale should be mounted on the handle in order to be able to sever the muscle/tendon tissue by choice at a particular depth.

To improve handling of the inventive cutting instrument and to provide secure cutting effect and/or dosage of the cutting effect, it is further proposed with the invention that the handle should be positioned at an angle to the instrument longitudinal axis. The handle can be advantageously set at an angle of 20 degrees to the instrument longitudinal axis with respect to the shaft.

Owing to this angled placement, better handling and actuation of the cutting mechanism are afforded during removal or severing of the quadriceps tendon, because with a linear arrangement of the handle as an extension of the shaft, the patient's body can impede actuation of the cutting instrument.

Further features and advantages of the invention can be inferred from the appended drawings, in which an embodiment of an inventive medical cutting instrument for cutting muscles and tendons is depicted only by way of example, without restricting the invention to this embodiment.

BRIEF DESCRIPTION OF THE DRAWINGS

FIG. 4 shows a view from behind and below the depiction in FIG. 3.

DETAILED DESCRIPTION OF THE INVENTION

Figure 1:
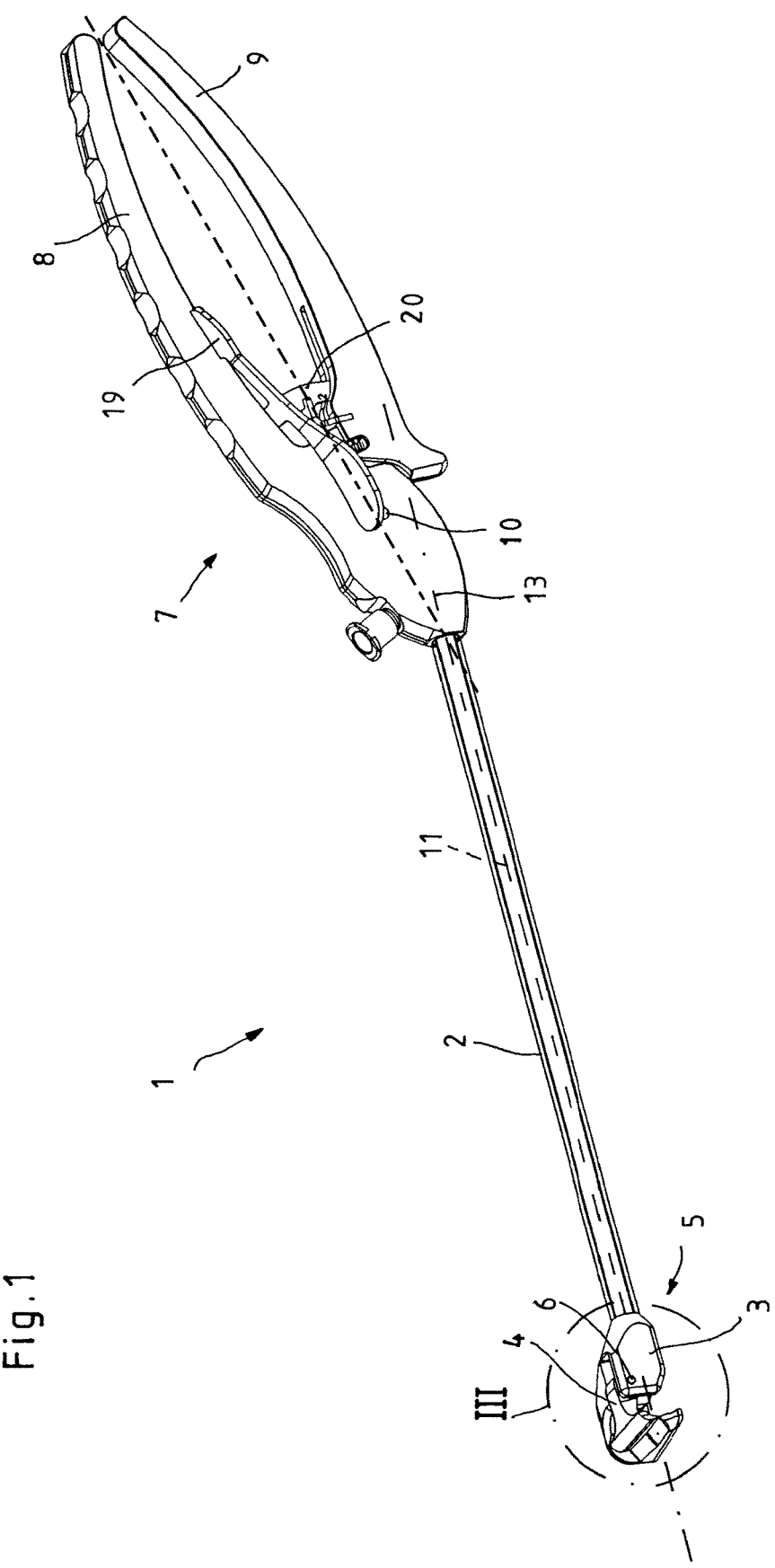
FIG. 1 shows a schematic side view of an inventive medical cutting instrument for cutting muscles and tendons.

FIG. 1 shows a perspective view of a medical cutting instrument 1 for cutting muscles and tendons.

This cutting instrument 1, configured for example as a punch for removing the quadriceps tendon, comprises a shaft 2 on whose distal end is mounted a tool 5 consisting of two jaw members 3 and 4, such that one jaw member 3 is of rigid configuration and the other jaw member 4 is configured as a jaw member 4 that can be pivoted with respect to the rigid jaw member 3 about a pivot axis 6. On the proximal end of the shaft 2 there is mounted a handle 7, which in the illustrated embodiment consists of two gripping members 8 and 9, such that one gripping member 8 is of rigid configuration and the other gripping member 9 is configured as a gripping member 9 that can be pivoted with respect to the rigid gripping member 8 about a pivot axis 10.

As can further be seen from FIG. 1, the handle 7 is not mounted in a straight-line formation extending the shaft 2 at the proximal end of the shaft 2, but rather is preferably set off at an angle of 20 degrees. Owing to this bending of the handle 7 with respect to the shaft 2, better handling and actuation of the cutting mechanism are possible in removing or severing the quadriceps tendon, because with a linear arrangement of the handle 7 extending the shaft 2, the patient's body can impede actuation of the cutting instrument.

Figure 2:
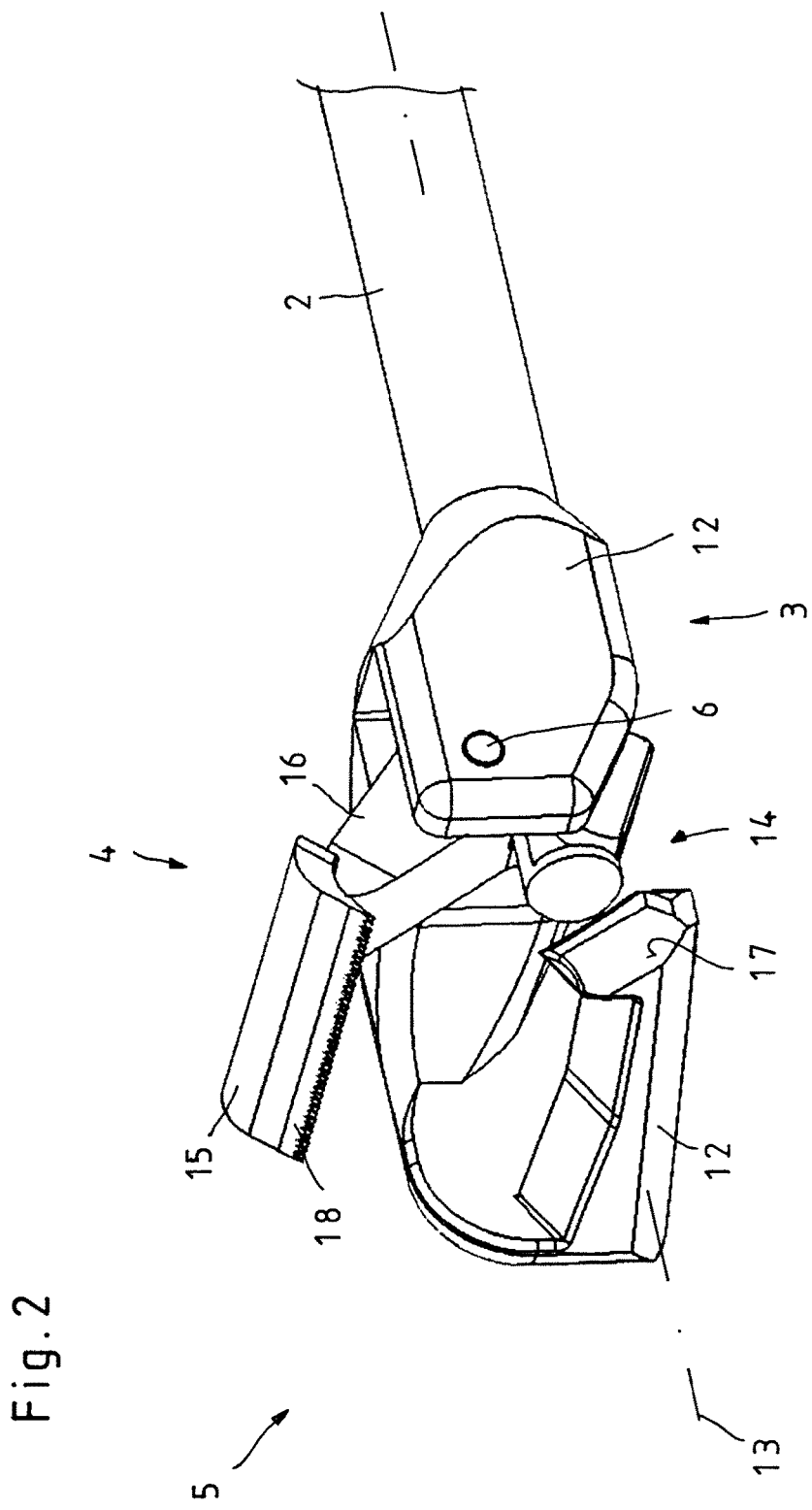
FIG. 2 shows an enlarged view of detail III from FIG. 1, but showing the tool in the opened state.

The pivotable jaw member 4 of the tool 5 and the pivotable gripping member 9 of the handle 7 operatively interact with one another by way of an actuation element 11 mounted in the shaft 2, in such a way that the pivotable jaw member 4 can be converted by actuation of the pivotable gripping member 9 between a closed position contiguous with the rigid jaw member 3 (FIGS. 1, 3 and 4) and an opened position pivoted with respect to the rigid jaw member 3 (FIG. 2). By means of the rigid jaw member 3, it is possible to achieve an especially advantageous guiding and thus positioning of the tendon during cutting, resulting in a substantially better cutting outcome in subcutaneous use of the cutting instrument 1.

Alternatively to the illustrated embodiment of the cutting instrument 1 with a rigid jaw member 3 and a pivotable jaw member 4, it is also possible of course to configure both jaw members as pivotable. A variant with two pivotable jaw members proves especially appropriate precisely for free-floating, freely dissectible tendons.

Moreover, the illustrated pivoting of the jaw member 4 with respect to the other jaw member 3 is only one embodiment for reciprocal displacement of the jaw members 3 and 4 with respect to one another. In addition to pivoting around the pivot axis 6, it is also possible, for example, as an alternative or in addition, to slide the jaw members 3 and 4 axially with respect to one another.

Figure 3:
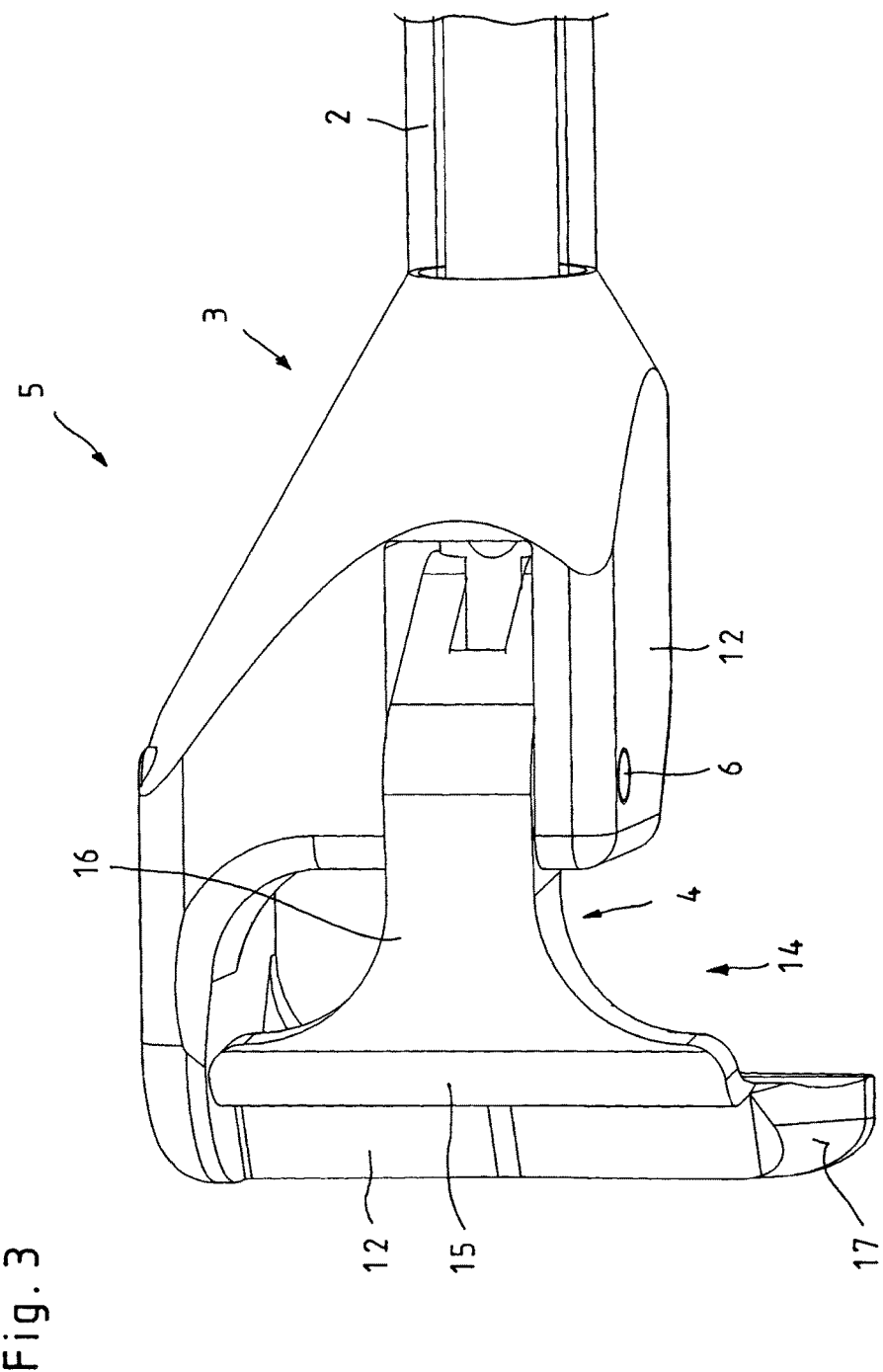
FIG. 3 shows an enlarged overhead view of detail III from FIG. 1.

The structure of the distal-end tool 5 consisting of the jaw members 3 and 4 can be seen, in particular, from the enlarged detail views in FIGS. 2 through 4.

As is especially clear from FIGS. 2 and 3, the rigid jaw member 3 in the overhead view is configured in a U-shape in such a way that both parallel legs 12 of the U are disposed diagonally to the instrument longitudinal axis 13 and the opening 14 of the U points to one side of the rigid jaw member 3.

The pivotable jaw member 4 seen from overhead is T-shaped in such a way that the crossing 15 of the T is disposed parallel to the distal-side leg 12 of the U-shaped rigid jaw member 3 and the longitudinal part 16 of the T is disposed as a continuation of the actuation element 11.

Owing to the configuration of the rigid jaw member 3 as a jaw member 3 open toward one side and owing to the T-shaped configuration of the pivotable jaw member 4, it is possible to push the tool 5 from the side onto the muscle/tendon tissue that is to be severed in order thereby to allow a controlled, final severing of the muscle/tendon tissue.

To facilitate lateral pushing of the rigid jaw member 3 onto the muscle/tendon tissue that is to be severed, a run-up slope 17 is configured on the free end of the distal-side leg 12 of the U-shaped rigid jaw member 3, as can be seen from FIG. 4.

To sever the muscle/tendon tissue, on the pivotable jaw member 4 a cutting edge 18 is mounted that is disposed oriented downward toward the rigid jaw member 3 on the distal-side crossing 15 of the pivotable jaw member 4 in such a way that the muscle/tendon tissue disposed between the jaw members 3 and 4 is severed as soon as the pivotable jaw member 4 of the tool 5 is completely closed.

Alternatively to the configuration of the cutting edge 18 only on the pivotable jaw member 4, it is also possible of course to provide preferably V-shaped cutting edges 18 both on the pivotable jaw member 4 and on the rigid jaw member 3.

As can be seen from FIG. 4, the cutting edge 18 is configured as toothed in the manner of a comb, so that the pivotable jaw member 4 can be mounted in controlled manner onto the previously split muscle/tendon tissue and holds and guides it until the muscle/tendon tissue is severed upon closing the jaw members 3 and 4.

As can be seen from FIG. 1, for adjusting and shifting the cutting depth a lever mechanism 19 is provided on the handle 7 that configures a variable stop for closing the two jaw members 3 and 4 with respect to one another and thus causes the shifting of the cutting depth.

In addition, on the handle 7 a scale 20 is provided that can be read from the outside, so that the muscle/tendon tissue can be severed by choice at a determined depth by actuation of the lever mechanism 19. Said lever mechanism 19 with the scale 20, together with the comb-like toothed cutting edge 18, allows a highly precise adjustment of the cutting depth with simultaneous exact placement of the cut that is to be effected.

Owing to the previously described configuration of the jaw members 3 and 4 of the medical cutting tool 1 as a laterally open tool 5, it becomes possible to push the rigid jaw member 3 in a controlled manner subcutaneously from the side onto the muscle/tendon tissue that is to be severed in order to be able to sever the muscle/tendon tissue definitively.

What is claimed is:

1. A medical cutting instrument for cutting muscles and tendons, comprising a shaft extending along a longitudinal axis between a proximal end and a distal end, a tool mounted on the distal end of the shaft, the tool having a pivotable jaw member and a rigid jaw member, wherein the pivotable jaw member can be pivoted with respect to the rigid jaw member, and having a handle that is mounted on the proximal end of the shaft, such that the pivotable jaw member and the handle operatively interact with one another by way of an actuation element mounted in the shaft, in such a way that the pivotable jaw member can be shifted by actuation of the handle between a closed position and an opened position of the tool, wherein the rigid jaw member from overhead is U-shaped and has:
a proximal leg extending along a first axis perpendicular to the longitudinal axis of the shaft between a first end and a second end,
a distal leg extending along a second axis perpendicular to the longitudinal axis of the shaft between a first end and a free second end, and a connecting portion extending between the first end of the proximal leg and the first end of the distal leg in a direction parallel to the longitudinal axis of the shaft, wherein the first end of the distal leg is directly connected to the connecting portion, wherein the rigid jaw member can be pushed laterally onto muscle/tendon tissue that is to be severed in such a way the muscle/tendon tissue that is to be severed is placed between the proximal leg and distal leg of the rigid jaw member and in that a cutting edge is configured on a distal end of the pivotable jaw member disposed transverse to the longitudinal axis and directed downward toward the rigid jaw member, wherein the pivotable jaw member has an axis of rotation extending in a direction parallel to the second axis.

2. The medical cutting instrument according to claim 1, wherein the cutting edge of the pivotable jaw member is V-shaped, and wherein the rigid jaw member has a V-shaped cutting edge.

3. The medical cutting instrument according to claim 1, wherein the cutting edge is of a toothed configuration.

4. The medical cutting instrument according to claim 1, wherein a run-up slope is configured on the free second end of the rigid jaw member.

5. The medical cutting instrument according to claim 1, wherein there is mounted in an area of the handle a lever mechanism that constitutes a variable stop for closing the jaw members with respect to one another and thus causes a shifting of a cutting depth.

6. The medical cutting instrument according to claim 5, wherein a scale is mounted on the handle to determine the cutting depth.

7. The medical cutting instrument according to claim 1, wherein the handle is disposed on the shaft at an angle to the longitudinal axis.

8. The medical cutting instrument according to claim 7, wherein the handle is disposed on the shaft at an angle of 20 degrees to the longitudinal axis.

9. A medical cutting instrument for cutting muscles and tendons, comprising:
- a shaft extending along a longitudinal axis between a proximal end of the shaft and a distal end of the shaft;
- a tool mounted on the distal end of the shaft having a pivotable jaw member and a rigid jaw member;
- a handle mounted on the proximal end of the shaft configured to move the pivotable jaw member relative to the rigid jaw member between a closed position and an opened position;
- the rigid jaw member having:
    - a proximal leg extending along a first axis perpendicular to the longitudinal axis of the shaft between a first end and a second end,
    - a distal leg extending along a second axis perpendicular to the longitudinal axis of the shaft between a first end and a free second end,
    - and a connecting portion extending between the first end of the proximal leg and the first end of the distal leg in a direction parallel to the longitudinal axis of the shaft; wherein the first end of the distal leg is directly connected to the connecting portion, and
- a cutting edge disposed on a distal end of the pivotable jaw member;
- wherein the pivotable jaw member has an axis of rotation extending in a direction parallel to the second axis.

* * * * *